United States Patent [19]

Jeffries

[11] Patent Number: 4,663,284

[45] Date of Patent: May 5, 1987

[54] PROCESS FOR ENHANCED FERMENTATION OF XYLOSE TO ETHANOL

[75] Inventor: Thomas W. Jeffries, Madison, Wis.

[73] Assignee: The United States of America as represented by the Secretary of Agriculture, Washington, D.C.

[21] Appl. No.: 650,462

[22] Filed: Sep. 14, 1984

[51] Int. Cl.$^4$ .................... C12P 7/06; C12P 7/14; C12P 7/08; C12N 1/16

[52] U.S. Cl. .................................. 435/161; 435/162; 435/163; 435/165; 435/255; 435/813; 435/911; 435/921

[58] Field of Search ............... 435/161, 162, 163, 165, 435/813, 911, 921, 255

[56] References Cited

U.S. PATENT DOCUMENTS

| | | | |
|---|---|---|---|
| 4,260,685 | 4/1981 | Pilipski | 435/161 |
| 4,350,765 | 9/1982 | Chibata et al. | 435/161 |
| 4,359,534 | 11/1982 | Kurtzman et al. | 435/161 |
| 4,368,268 | 1/1983 | Gong | 435/161 |
| 4,472,501 | 9/1984 | Takasawa et al. | 435/165 |
| 4,477,569 | 10/1984 | Schneider et al. | 435/161 |
| 4,511,656 | 4/1985 | Gong | 435/161 |
| 4,567,145 | 1/1986 | Faber et al. | 435/161 |

OTHER PUBLICATIONS

*The Yeasts,* Lodder (Ed.), (1970), North-Holland Publishing Co. Amsterdam, pp. 355-357.

Jeffries, "Biotechnol. Bioeng. Symp.", 12: 103-110 (1982).

*Primary Examiner*—Robert J. Warden
*Assistant Examiner*—Patricia Kate White
*Attorney, Agent, or Firm*—M. Howard Silverstein; David G. McConnell

[57] ABSTRACT

Ethanol is produced from D-xylose by fermentation with any of the known xylose-metabolizing yeasts, such as *Pachysolen tannophilus*. To improve the yield of ethanol, small quantities of glucose are added to the fermentation medium during the fermentation process.

7 Claims, No Drawings

PROCESS FOR ENHANCED FERMENTATION OF XYLOSE TO ETHANOL

FIELD OF THE INVENTION

This invention relates to a process for the production of ethanol by enhanced fermentation of xylose.

BACKGROUND OF THE INVENTION

In recent years there has been great interest in the conversion of biomass to ethanol since ethanol is valuable both as a chemical feedstock and as fuel. Although ethanol can be produced from such biomass materials as molasses and corn, potentially the most attractive process for producing ethanol from biomass uses as its starting material lignocellulose products, such as wood waste products, which are much cheaper than the other biomass starting materials and are available in extremely large quantities. It is known that lignocellulosic materials can be converted to ethanol by a two-step process comprising an acid or enzymatic prehydrolysis of the lignocellulosic materials to a mixture of sugars, the most important of which is D-xylose, followed by fermentation of the xylose to ethanol using any one of a number of yeasts known to be capable of effecting this transformation.

Known prior art in this field includes U.S. Pat. No. 4,260,685 issued Apr. 7, 1981 to Pilipski. This patent discloses a method for effecting saccharification of raw cellulosic material using anhydrous liquid hydrogen chloride to yield usable glucose and other products, which in the case of many cellulosic materials comprising glucose and xylose will include D-xylose. The patent states that its products are intended for enzymatic degradation to produce alcohol.

U.S. Pat. No. 4,359,534 issued Nov. 16, 1982 to Kurtzman et al, and assigned to the same assignee as this application, describes a process for fermenting D-xylose to ethanol using the yeast *Pachysolen tannophilus*. The substrate used in this fermentation may be a mixture of D-xylose and glucose.

U.S. Pat. No. 4,368,268 issued Jan. 11, 1983 to Gong describes a process for the direct fermentation of D-xylose to ethanol using yeast mutants of various Candida species, including C. XF-217. The process can be either aerobic or anaerobic, and the substrate may comprise a mixture of D-glucose and D-xylose.

Besides the yeasts mentioned in the above patents, several other yeasts have been shown in recent years to be capable of converting D-xylose to ethanol. Except for *Pachysolen tannophilus*, these yeasts only effect fermentation of D-xylose to ethanol under aerobic conditions, and even in the case of *P. tannophilus* the fermentation proceeds faster aerobically. However, in none of the known processes does the yield of ethanol approach the theoretical limit of 0.51 parts by weight of ethanol per part by weight of xylose starting material. It is believed (although this invention is in no way limited by this belief) that the low yield of ethanol is largely due to oxidation of ethanol by respiration of the ethanol by the yeast. Indeed, it has been shown experimentally that when D-xylose is fermented aerobically with *P. tannophilus*, ethanol is formed and consumed throughout the fermentation.

It might be thought that the reduction in the yield of ethanol due to respiration by the yeast could be overcome by carrying out fermentation with *P. tannophilus* anaerobically, and thus in the absence of the oxygen necessary for respiration. However, not only does anaerobic fermentation with *P. tannophilus* suffer from the disadvantages of lack of growth and relatively slow fermentation already mentioned, but in such anaerobic fermentation the yield of ethanol decreases because of an increased production of the undesired by-product xylitol.

There is thus a need for a process for fermenting D-xylose which gives higher yields of ethanol from xylose than the prior art processes discussed above, and this invention seeks to provide such a process.

SUMMARY OF THE INVENTION

This invention provides a process for the production of ethanol in which a fermentation medium comprising D-xylose is aerobically fermented with a yeast capable of converting D-xylose to ethanol. In the instant process, glucose is added to the fermentation medium after the fermentation has commenced.

DETAILED DESCRIPTION OF THE INVENTION

As stated above, in the present invention glucose is added to the fermentation medium after the fermentation has commenced. It has been found that this addition of glucose increases the apparent yield of ethanol from D-xylose. The exact mechanism by which the glucose acts is not known, but it is believed (although the invention is in no way limited by this belief) that the addition of glucose results in repression of ethanol oxidation. The glucose addition may also shift the fermentation products in favor of ethanol and decrease the amount of the unwanted by-product xylitol produced. It is surprising that the addition of glucose increases ethanol yield without reducing the rate of xylose utilization, since in general glucose is known to be used by yeasts in preference to other carbohydrates present in a fermentation medium, so that prima facie one would expect glucose to be consumed completely before xylose was utilized by the microorganisms, with a concomitant decrease in the rate of utilization of xylose. No such reduction has been found to occur.

In the instant method it is preferred that a plurality of additions of glucose be made to the fermentation medium at intervals during the fermentation; since the glucose is consumed by the yeast during the fermentation, a plurality of additions of glucose at intervals during the fermentation helps to ensure that some concentration of glucose is present throughout the fermentation so that the beneficial effects of glucose in increasing ethanol yield are sustained throughout the fermentation. In general, it is preferred that the intervals between successive additions of glucose be not greater than about 24 hours and that the amount of glucose added to the fermentation medium at any one addition not exceed about one percent by weight of the fermentation medium. Indeed, it is especially preferred that the intervals between successive additions of glucose be not greater than about twelve hours and that the amount of glucose added to the fermentation medium to any one addition not exceed about 0.5 percent by weight of the fermentation medium. Naturally, smaller amounts of glucose can be added at intervals of less than twelve hours and indeed glucose can be continuously added to the fermentation during the fermentation. Desirably, the addition of glucose is made either at intervals or continuously until substantially all the D-xylose is consumed and the maximum ethanol concentration is attained.

The yeast used in the instant process may be any of the various species of yeast known to be capable of fermenting D-xylose to ethanol. Thus, the yeast may be a yeast of the genus Candida (for example *C. tropicalis, C.* XF 217, *C. shehatae* and others), *Kluyveromyces marxianus,* or *Pachysolen tannophilus,* with *P. tannophilus* being especially preferred. A complete taxonomic description of *P tannophilus* is given in the aforementioned U.S. Pat. No. 4,359,534 to Kurtzman et al, the entire disclosure of which is herein incorporated by reference. Obviously, the fermentation medium must contain, in addition to D-xylose, the appropriate nutrients for growth of the yeast used; however, since the nutrients required for growth of any of these known yeast will be apparent to those skilled in the art, it is unnecessary here to discuss these other nutrients. Equally, the optimum temperature for conversion of D-xylose to ethanol by any particular yeast will be known to those skilled in the art or can readily be determined by routine empirical tests. In general, a temperature of approximately 32° C. gives good results. Preferably, the aerobic fermentation is conducted under low aeration conditions. For example, when 50 ml. aliquots of fermentation medium are confined in 125 ml. Erlenmeyer flasks, an appropriate low aeration condition may be provided by shaking the flasks at 100 rpm. using a 2.5 cm. diameter stroke. It is believed that those skilled in the art will have no difficulty scaling up such aeration conditions to larger quantities of fermentation medium.

The D-xylose used as the starting material in the instant process can be in the form of the pure sugar. However, for economic reasons it is generally desirable to use D-xylose in the form of a hydrolysate of a natural lignocellulosic material, for example an acid or enzymatic material hydrolysate of hemicellulose. In most cases, such hydrolysates will already contain small amounts of glucose; if, however, either pure D-xylose or a hydrolysate which does not contain any significant quantity of glucose is used as the starting material in the instant process, it is generally desirable to add a small quantity of glucose e.g. 0.5 percent by weight of the fermentation medium to the fermentation medium before fermentation commences, in order that the beneficial effects of glucose will be present throughout the fermentation.

The following example is now given, though by way of illustration only, to show details of particularly preferred materials and techniques used in the instant process.

EXAMPLE

*Pachysolen tannophilus,* Boidin et Adzet, NRRL Y-2460 (ATCC 32691) was obtained from the yeast collection at the United States Department of Agriculture, Northern Region Research Center, Peoria, Ill. and maintained on yeast malt agar. Cultures were grown for three days at 32° C. and stored at 5° C. The experiments described below used as the fermentation medium an aqueous medium containing 0.17% yeast nitrogen base without ammonium sulfate or amino acids (obtained from Difco) to which 0.227% urea was added as a nitrogen source. The medium were prepared by combining autoclaved sugar solutions with filter-sterilized yeast base and urea. Aeration was effected by shaking 50 ml. aliquots of media in a 125 ml. Erlenmeyer flask at 100 rpm. using a 2.5 cm. diameter stroke. Each experiment was conducted using three separate flasks, together with, where necessary, a fourth flask which was a "sacrificial" flask used to replenish the volumes of the other three flasks to restore the original volume after sampling. Ethanol concentrations were determined by gas chromatography according to the method of Jeffries, Biotechnol. Bioeng. Symp., 12:103–110 (1982).

Four separate sets of flasks were used in the experiment. The first set of flasks used a medium containing 4.5% xylose and no glucose. The second set contained 4.5% glucose and no xylose. The third set contained 3% xylose and 1.5% glucose, all the of the glucose and xylose being present in the flask initially. The fourth set initially contained 3% xylose plus 0.5% glucose, but additional quantities of glucose, each sufficient to produce a glucose concentration of 0.5% in the solution, were added 1 and 2 days after the experiment began. The flasks were allowed to ferment in an environment maintained at room temperature and the ethanol concentration determined daily for seven days.

As would be expected, the second set of flasks, containing glucose alone, showed a rapid and efficient fermentation. A peak ethanol concentration in excess of 400 mM was obtained after only 2 days and represented conversion of glucose to ethanol at 84% of theoretical efficiency. In contrast, the first set of flasks containing xylose alone only achieved a peak ethanol concentration of about 270 mM after 5 days, representing conversion of xylose to ethanol at only 55% of the theoretical maximum. In the third series of flasks, the presence of 1.5% of glucose at the beginning of the experiment had relatively little effect on the efficiency of xylose conversion; the results obtained were substantially those which would be anticipated for concurrent, but separate, fermentation of the appropriate quantities of xylose and glucose.

In contrast, the fourth series of flasks, to which glucose was periodically added, attained a higher ethanol concentration than the third set, in which all the glucose was present at the beginning of the experiment. The fourth series of flasks obtained a peak ethanol concentration of approximately 400 mM after 4 days. This ethanol concentration represented 83% of the theoretical maximum obtained from the total quantities of xylose and glucose present in the flasks. Thus, assuming that the efficiency of glucose utilization in the fourth set of flasks was the same as in the second, namely 84%, the conversion of xylose to ethanol in the fourth series of flasks, in accordance with the instant method, amounted to 81% of theoretical, a great improvement on the efficiencies achieved in the first and third series of flasks.

It will be apparent to those skilled in the art the numerous changes and modifications can be made in the embodiments of the invention described above without departing from the scope of the invention. Accordingly, the whole of the foregoing description is to be construed in an illustrative and not in a limitative sense, the scope of the invention being defined solely by the appended claims.

I claim:

1. A process for the production of ethanol, which process comprises:
   (a) aerobically fermenting D-xylose in a fermentation medium comprising D-xylose with a yeast having the ability to convert D-xylose to ethanol; and
   (b) adding glucose to said fermentation medium after said fermenting has commenced and during said fermenting with the adding being continuously or by successive addition at intervals during said fermenting and with said intervals between successive addition being not greater than about 24 hours and wherein the amount of the glucose added continuously or by additions does not bring the glucose concentration to exceed about 1 percent by weight of the fermentation medium.

2. A process according to claim 1 wherein said adding is by said successive additions and said intervals between the successive additions of glucose are not greater than about twelve hours and the amount of glucose added to said fermentation medium at any one addition does not exceed about 0.5 percent by weight of said fermentation medium.

3. A process according to claim 1 wherein said yeast is selected from the group consisting of Candida spp., *Kluyveromyces marxianus* and *Pachysolen tannophilus.*

4. A process according to claim 1 wherein said yeast is Pachysolen tannophilus.

5. A process according to claim 1 wherein said D-xylose is present in the form of an acid or enzymatic hydrolysate of hemicellulose.

6. A process for the production of ethanol, which process comprises:
  (a) fermenting a fermentation medium comprising D-xylose with *Pachysolen tannophilus,* having deposit accession numbers NRRL Y-2460 and ATCC 32691, and
  (b) making a plurality of additions of glucose to said fermentation medium at intervals during said fermenting, the intervals between successive additions of glucose being not greater than about twelve hours and with the amount of glucose in each addition not exceeding about 0.5 percent by weight of said fermentation medium and being the amount providing a glucose concentration in said fermentation medium not exceeding about 0.5 percent of said fermentation medium.

7. A process for producing an enhanced ethanol yield by aerobically fermenting D-xylose in a fermentation medium with *Pachysolen tannophilus* having deposit accession numbers NRRL Y-2460 and ATCC 32691 wherein the improvement comprises adding glucose to said fermentation medium after said fermentation has commenced and during the carrying forth of said fermentation with the adding being continuously or at intervals during each 24 hours of the carrying forth of said fermentation and being of an amount of the glucose providing a glucose concentration not exceeding one percent by weight of the fermentation medium until substantially all D-xylose is consumed.

* * * * *